(12) United States Patent
Press et al.

(10) Patent No.: US 8,183,281 B2
(45) Date of Patent: May 22, 2012

(54) CXC-CHEMOKINE RECEPTOR LIGANDS

(75) Inventors: Neil John Press, Horsham (GB); Simon James Watson, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/451,876

(22) PCT Filed: Jun. 4, 2008

(86) PCT No.: PCT/EP2008/056902
§ 371 (c)(1),
(2), (4) Date: Dec. 3, 2009

(87) PCT Pub. No.: WO2008/148790
PCT Pub. Date: Dec. 11, 2008

(65) Prior Publication Data
US 2010/0125071 A1    May 20, 2010

(30) Foreign Application Priority Data
Jun. 6, 2007   (EP) .................................. 07109704

(51) Int. Cl.
*A61K 31/341* (2006.01)
*A61K 31/381* (2006.01)
*C07D 339/04* (2006.01)
*C07D 339/06* (2006.01)
*C07D 333/04* (2006.01)
*C07D 333/46* (2006.01)
*C07D 307/12* (2006.01)

(52) U.S. Cl. ........ 514/438; 514/439; 514/447; 514/463; 514/471; 549/34; 549/35; 549/75; 549/492

(58) Field of Classification Search .................. 549/34, 549/35, 75, 492
See application file for complete search history.

(56) References Cited

U.S. PATENT DOCUMENTS
6,166,050 A    12/2000 Lombardo et al.
2004/0147559 A1    7/2004 Taveras et al.

FOREIGN PATENT DOCUMENTS
WO    WO 02/057230    7/2002
WO    WO 02/083624    10/2002
WO    WO 03/080053    10/2003
WO    WO 2004/011418    2/2004

OTHER PUBLICATIONS

Idiopathic pulmonary fibrosis [online] retrieved from the internet on Nov. 10, 2010 URL; http://www.nlm.nih.gov/medlineplus/ency/article/000069.htm.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Asthma [online] retrieved from the internet on May 20, 2011 [URL; http://www.ncbi.nlm.nih.gov/pubmedhealth/PMH0001196/].*
COPD [online] retrieved from the internet of May 20, 2011 [URL; http://www.ncbi.nlm.nih.gov/pubmedhealth/PMH0001153/].*
Yun Feng Xie, "Structure-Activity Relationships of Novel, Highly Potent, Selective, and Orally Active CCR1 Antagonists" Bioorg. Med. Chem. Lett. 17:3367-3372, 2007.
J. Robert Merritt et al., "Synthesis and Structure-Activity Relationships of 3,4-diaminocyclobut-3-ene-1,2-dione CXCR2 Antagonists" *Bioorganic and Medicinal Chemistry Letters* 16:4107-4110, Sep. 2006.

* cited by examiner

*Primary Examiner* — Shawquia Young
(74) *Attorney, Agent, or Firm* — Mark W. Milstead

(57) ABSTRACT

The present invention relates to compounds of formula (I) with the substituents as defined herein, and uses thereof.

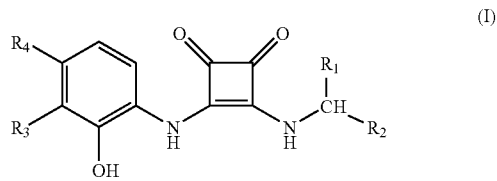

6 Claims, No Drawings

CXC-CHEMOKINE RECEPTOR LIGANDS

The present invention relates to organic compounds, e.g. compounds of formula (I), and uses thereof.

In one aspect the present invention provides a compound of formula

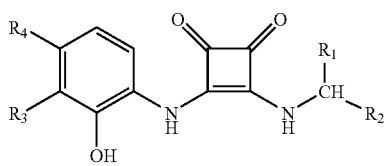

(I)

wherein
R$_1$ is hydrogen or (C$_{1-8}$)alkyl, and
R$_2$ is a non-aromatic 5-membered unsubstituted or one- or morefold substituted heterocyclic ring system having 1 to 4 heteroatoms selected from O, S; or
R$_1$ and R$_2$, together with the —CH group to which they are attached form a non-aromatic 5-membered unsubstituted or one- or morefold substituted heterocyclic ring system having 1 to 4 heteroatoms selected from O, S,
R$_3$ is hydrogen, halogen, cyano, (C$_{1-8}$)alkyl, (C$_{1-8}$)alkoxy, amino, (C$_{1-8}$)alkylamino, di(C$_{1-8}$)alkylamino, (C$_{1-8}$)alkylaminocarbonyl, di(C$_{1-8}$)alkylaminocarbonyl, aminosulfonyl, (C$_{1-8}$)alkylaminosulfonyl, di(C$_{1-8}$)alkylaminosulfonyl, (C$_{1-8}$)alkylsulfonyl, heterocyclylcarbonyl or heterocyclylsulfonyl, wherein heterocyclyl is a 5 or 6 membered unsubstituted or one- or morefold substituted ring system having 1 to 4 heteroatoms selected from N, O, S,
R$_4$ is hydrogen, halogen or cyano.

In another aspect the present invention provides a compound of formula (I) wherein
R$_1$ is hydrogen, methyl or ethyl, and
R$_2$ is a non-aromatic 5-membered unsubstituted or one- or morefold substituted heterocyclic ring system having 1 heteroatom selected from O, S; or
R$_1$ and R$_2$ together with the —CH group to which they are attached form a non-aromatic 5-membered unsubstituted or onefold substituted heterocyclic ring system having 1 heteroatom selected from O, S, wherein the substituent is methyl or oxo,
R$_3$ is hydrogen, di(C$_{1-2}$)alkylaminocarbonyl, di(C$_{1-4}$)alkylaminosulfonyl, (C$_{1-2}$)alkylsulfonyl, heterocyclylcarbonyl or heterocyclylsulfonyl, wherein heterocyclyl is a 5 or 6 membered unsubstituted or one- or morefold substituted ring system having 1 to 2 heteroatoms selected from N, O,
R$_4$ is hydrogen or chloro.

In another aspect the present invention provides a compound of formula (I) selected from the group consisting of
3-{3,4-Dioxo-2-[(tetrahydrofuran-2-ylmethyl)-amino]-cyclobut-1-enylamino}-2-hydroxy-N,N-dimethyl-benzamide,
6-Chloro-2-hydroxy-N,N-dimethyl-3-{2-[(R)-1-((2R,5R)-5-methyl-tetrahydrofuran-2-yl)-propylamino]-3,4-dioxo-cyclobut-1-enylamino}-benzenesulfonamide,
6-Chloro-2-hydroxy-N,N-dimethyl-3-{2-[(R)-1-(2R,5R)-5-methyl-tetrahydrofuran-2-yl)-propylamino]-3,4-dioxo-cyclobut-1-enylamino}-benzenesulfonamide,
3-[3,4-Dioxo-2-(tetrahydrothiophen-3-ylamino)-cyclobut-1-enylamino]-2-hydroxy-N,N-dimethyl-benzamide,
6-Chloro-3-[3,4-dioxo-2-(tetrahydrothiophen-3-ylamino)-cyclobut-1-enylamino]-2-hydroxy-N,N-dimethyl-benzenesulfonamide,
4-{6-Chloro-3-[3,4-dioxo-2-(tetrahydrothiophen-3-ylamino)-cyclobut-1-enylamino]-2-hydroxy-benzenesulfonyl}-piperazine-1-carboxylic acid tert-butyl ester,
3-[4-Chloro-2-hydroxy-3-(morpholine-4-sulfonyl)-phenylamino]-4-(tetrahydro-thiophen-3-ylamino)-cyclobut-3-ene-1,2-dione,
3-[4-Chloro-2-hydroxy-3-(4-methyl-piperazine-1-sulfonyl)-phenylamino]-4-tetrahydro-thiophen-3-ylamino)-cyclobut-3-ene-1,2-dione,
3-(4-Chloro-2-hydroxy-phenylamino)-4-(tetrahydrothiophen-3-ylamino)-cyclobut-3-ene-1,2-dione,
3-{3,4-Dioxo-2-[((R)-5-oxo-tetrahydrofuran-2-ylmethyl)-amino]-cyclobut-1-enylamino}-2-hydroxy-N,N-dimethyl-benzamide,
3-{3,4-Dioxo-2-[(R)-(tetrahydrofuran-3-yl)amino]-cyclobut-1-enylamino}-2-hydroxy-N,N-dimethyl-benzamide,
3-{3,4-Dioxo-2-[(S)-(tetrahydrofuran-3-yl)amino]-cyclobut-1-enylamino}-2-hydroxy-N,N-dimethyl-benzamide,
2-Hydroxy-N,N-dimethyl-3-{2-[(R)-1-((2S,5S)-5-methyl-tetrahydrofuran-2-yl)-propylamino]-3,4-dioxo-cyclobut-1-enylamino}-benzamide,
4-(6-Chloro-2-hydroxy-3-{2-[(R)-1-((2R,5R)-5-methyl-tetrahydrofuran-2-yl)-propylamino]-3,4-dioxo-cyclobut-1-enylamino}-benzene sulfonyl)-piperazine-1-carboxylic acid tert-butyl ester,
3-[4-Chloro-2-hydroxy-3-(morpholine-4-sulfonyl)-phenylamino]-4-[(R)-1-((2R,5R)-5-methyl-tetrahydrofuran-2-yl)-propylamino]-cyclobut-3-ene-1,2-dione,
6-Chloro-N-ethyl-2-hydroxy-N-methyl-3-{2-[(R)-1-((2R,5R)-5-methyl-tetrahydrofuran-2-yl)-propylamino]-3,4-dioxo-cyclobut-1-enylamino}-benzenesulfonamide,
3-[4-Chloro-2-hydroxy-3-(pyrrolidine-1-sulfonyl)-phenylamino]-4-[(R)-1-((2R,5R)-5-methyl-tetrahydrofuran-2-yl)-propylamino]-cyclobut-3-ene-1,2-dione,
6-Chloro-N-ethyl-2-hydroxy-3-{2-[(R)-1-((2R,5R)-5-methyl-tetrahydrofuran-2-yl)-propylamino]-3,4-dioxo-cyclobut-1-enylamino}-benzenesulfonamide,
3-[4-Chloro-2-hydroxy-3-(4-methyl-piperazine-1-sulfonyl)-phenylamino]-4-[(R)-1-((2R,5R)-5-methyl-tetrahydrofuran-2-yl)-propylamino]-cyclobut-3-ene-1,2-dione,
6-Chloro-N,N-diethyl-2-hydroxy-3-{2-[(R)-1-((2R,5R)-5-methyl-tetrahydrofuran-2-yl)-propylamino]-3,4-dioxo-cyclobut-1-enylamino}-benzenesulfonamide,
2-Hydroxy-N,N-dimethyl-3-{2-[(R)-1-((2R,5R)-5-methyl-tetrahydrofuran-2-yl)-propylamino]-3,4-dioxo-cyclobut-1-enylamino}-benzene sulfonamide,
6-Chloro-3-{3,4-dioxo-2-[(S)-(tetrahydrofuran-3-yl)amino]-cyclobut-1-enylamino}-2-hydroxy-N,N-dimethyl-benzene sulfonamide,
N,N-Diethyl-2-hydroxy-3-{2-[(R)-1-((2R,5R)-5-methyl-tetrahydrofuran-2-yl)-propylamino]-3,4-dioxo-cyclobut-1-enylamino}-benzamide,
3-(4-Chloro-2-hydroxy-3-methanesulfonyl-phenylamino)-4-(tetrahydrothiophen-3-ylamino)-cyclobut-3-ene-1,2-dione,
3-(4-Chloro-2-hydroxy-3-methanesulfonyl-phenylamino)-4-[(R)-1-((2R,5R)-5-methyl-tetrahydrofuran-2-yl)-propylamino]-cyclobut-3-ene-1,2-dione,
3-[4-Chloro-2-hydroxy-3-(piperazine-1-sulfonyl)-phenylamino]-4-[(R)-1-((2R,5R)-5-methyl-tetrahydrofuran-2-yl)-propylamino]-cyclobut-3-ene-1,2-dione, 3-Chloro-2-(piperazine-1-sulfonyl)-6-(tetrahydrothiophen-3-ylamino)-phenol,
6-Chloro-N-ethyl-2-hydroxy-N-isopropyl-3-{2-[(R)-1-((2R,5R)-5-methyl-tetrahydrofuran-2-yl)-propylamino]-3,4-dioxo-cyclobut-1-enylamino}-benzenesulfonamide,
2-Hydroxy-N,N-dimethyl-3-{2-[(R)-1-((2R,5R)-5-methyl-tetrahydrofuran-2-yl)-propylamino]-3,4-dioxo-cyclobut-1-enylamino}-benzamide,
3-[4-Chloro-2-hydroxy-3-(4-isopropyl-piperazine-1-sulfonyl)-phenylamino]-4-[(R)-1-((2R,5R)-5-methyl-tetrahydrofuran-2-yl)-propylamino]-cyclobut-3-ene-1,2-dione,
3-[4-Chloro-3-(4-cyclopropyl-piperazine-1-sulfonyl)-2-hydroxy-phenylamino]-4-[(R)-1-((2R,5R)-5-methyl-tetrahydrofuran-2-yl)-propylamino]-cyclobut-3-ene-1,2-dione,
3-[4-Chloro-2-hydroxy-3-(4-isopropyl-3-methyl-piperazine-1-sulfonyl)-phenylamino]-4-[(R)-14(2R,5R)-5-methyl-tetrahydrofuran-2-yl)-propylamino]-cyclobut-3-ene-1,2-dione,
3-[3-(4-tert-Butyl-piperazine-1-sulfonyl)-4-chloro-2-hydroxy-phenylamino]-4-[(R)-1-((2R,5R)-5-methyl-tetrahydrofuran-2-yl)-propylamino]-cyclobut-3-ene-1,2-dione,
3-[4-Chloro-2-hydroxy-3-(4-propyl-piperazine-1-sulfonyl)-phenylamino]-4-[(R)-1-((2R,5R)-5-methyl-tetrahydrofuran-2-yl)-propylamino]-cyclobut-3-ene-1,2-dione,
3-[4-Chloro-3-(4-ethyl-3-methyl-piperazine-1-sulfonyl)-2-hydroxy-phenylamino]-4-[(R)-1-((2R,5R)-5-methyl-tetrahydrofuran-2-yl)-propylamino]-cyclobut-3-ene-1,2-dione,
3-[3-(5-Benzyl-2,5-diaza-bicyclo[2.2.1]heptane-2-sulfonyl)-4-chloro-2-hydroxy-phenylamino]-4-[(R)-1-((2R,5R)-5-methyl-tetrahydrofuran-2-yl)-propylamino]-cyclobut-3-ene-1,2-dione,
6-Chloro-2-hydroxy-N-methyl-3-{2-[(R)-1-((2R,5R)-5-methyl-tetrahydrofuran-2-yl)-propylamino]-3,4-dioxo-cyclobut-1-enylamino}-benzenesulfonamide, and
2-Hydroxy-N,N-dimethyl-3-{2-[(R)-1-((2R,5S)-5-methyl-tetrahydrofuran-2-yl)-propylamino]-3,4-dioxo-cyclobut-1-enylamino}-benzamide.

In another aspect the present invention provides a compound of formula (I), which is a compound of formula

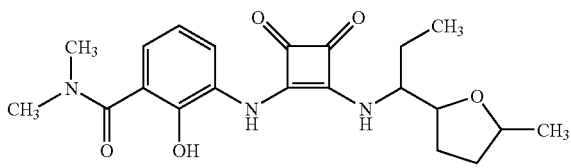

(I$_{EX}$)

or of formula

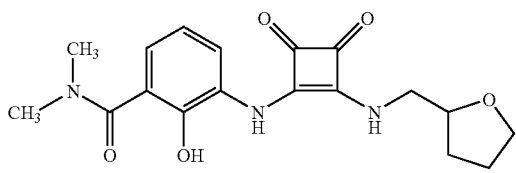

(II$_{EX}$)

If not otherwise defined herein
alkyl includes linear or branched $(C_{1-8})$alkyl, such as $(C_{1-6})$alkyl or $(C_{1-4})$alkyl, e.g. $(C_{1-2})$alkyl, including unsubstituted or substituted alkyl, e.g. alkyl substituted by groups which are conventional in organic chemistry, e.g. halogen, OH, $NH_2$ or halo$(C_{1-6})$alkyl,
halogen includes fluoro, chloro, bromo, iodo, e.g. fluoro, chloro, bromo, preferably chloro,
heterocyclyl includes heterocyclyl having 5 or 6 ring members and 1 to 4 heteroatoms selected from N, O, S, preferably N, O, such as alicyclic and aromatic heterocyclyl, e.g. heterocyclyl having 6 ring members and 1 to 2 heteroatoms selected from N, O, S; e.g. $R_1$ and $R_2$ together with the —CH group to which they are attached form tetrahydrofuranyl, such as tetrahydrofuran-2-yl, tetrahydrofuran-3-yl, 5-methyltetrahydrofuran-2-yl, or tetrahydrothiophen, such as tetrahydrothiophen-3-yl. $R_3$ can be heterocyclylsulfonyl, e.g.
piperazinsulfonyl, such as unsubstituted piperazin-1-sulfonyl, 4-methyl-piperazin-1-sulfonyl, 4-propyl-piperazin-1-sulfonyl, 4-cyclopropyl-piperazin-1-sulfonyl, 3-methyl-4-ethyl-piperazin-1-sulfonyl 4-(iso-propyl)-piperazin-1-sulfonyl, 4-(t-butylcarbonyl)-piperazin-1-sulfonyl,
pyrrolidinsulfonyl, such as pyrrolidin-1-sulfonyl,
bridged heterocyclyl, such as e.g. 2,5-diazabicyclo[2.2.1]-heptan-2-sulfonyl.

In a compound of formula (I) each single defined substitutent may be a preferred substituent, e.g. independently of each other substitutent defined, e.g.
$R_3$ is hydrogen and $R_1$, $R_2$ and $R_4$ are as defined above, or
$R_3$ is dialkylaminosulfonyl and $R_1$, $R_2$ and $R_4$ are as defined above, or
$R_3$ is dialkylaminocarbonyl and $R_1$, $R_2$ and $R_4$ are as defined above, or
$R_3$ is heterocyclylsulfonyl and $R_1$, $R_2$ and $R_4$ are as defined above, or
$R_3$ is alkylsulfonyl and $R_1$, $R_2$ and $R_4$ are as defined above, or
$R_2$ is non-aromatic 5-membered heterocyclyl having 1 heteroatom selected from O, S and
$R_1$, $R_3$ and $R_4$ are as defined above.

Compounds of formula (I) in free or pharmaceutically acceptable salt form are hereinafter referred to alternatively as compounds of the invention.

A compound of the present invention may exist in the form of isomers and mixtures thereof; e.g. optical isomers, diastereoisomers, cis/trans isomers. A compound of the present invention may e.g. contain asymmetric carbon atoms and may thus exist in the form of enantiomers or diastereoisomers and mixtures thereof, e.g. racemates. Substituents at any asymmetric carbon atom may be present in the (R)-, (S)- or (R,S)-configuration, preferably in the (R)- or (S)-configuration. E.g. cis/trans isomers may be present, in case that an aliphatic double bond is present in a compound of the present invention. Isomeric mixtures may be separated as appropriate, e.g. according, e.g. analogously, to a method as conventional, to obtain pure isomers. The present invention includes a compound of the present invention in any isomeric form and in any isomeric mixture.

Any compound described herein, e.g. a compound of the present invention, may be prepared as appropriate, e.g. according, e.g. analogously, to a method as conventional, e.g. or as specified herein. Starting materials are known or may be prepared according, e.g. analogously, to a method as conventional or as described herein.

A compound of formula I thus obtained may be converted into another compound of formula I, e.g. or a compound of formula I obtained in free form may be converted into a salt of a compound of formula I and vice versa.

Any compound described herein, e.g. a compound of the present invention, may be prepared as appropriate, e.g. according, e.g. analogously, to a method as conventional, e.g. or as specified herein. Starting materials are known or may be prepared according, e.g. analogously, to a method as conventional or as described herein.

In another aspect the present invention provides a process for the preparation of a compound of the present invention comprising reacting a compound of formula

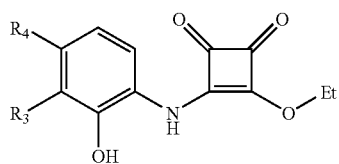

wherein $R_3$ and $R_4$ are as defined above, with a compound of formula

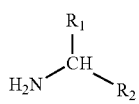

wherein $R_1$ and $R_2$ are as defined above, under appropriate conditions, e.g. in the presence of triethylamine, acetonitrile, methanol, for an appropriate time, e.g. 2 to 24 hours, at appropriate temperatures, e.g. room temperature, to obtain a compound of formula (I) of the invention.

A compound of formula I thus obtained may be converted into another compound of formula I, e.g. or a compound of formula I obtained in free form may be converted into a salt of a compound of formula I and vice versa.

Compounds of the invention, are useful as pharmaceuticals.

Accordingly the invention also provides a compound of formula I in free or pharmaceutically acceptable salt form for use as a pharmaceutical.

In another aspect the present invention provides the use of a compound of formula (I) wherein the substituents are as defined above as a pharmaceutical.

The compounds of the invention act as CXCR2 receptor antagonists, thereby inhibiting the infiltration and activation of inflammatory cells, in particular neutrophils, monocytes and CD8+ T cells and mediators involved in chronic obstructive pulmonary disease (COPD). The compounds of the invention therefore provide symptomatic relief and reduce disease progression.

The airways of subject with COPD exhibit an inflammatory response which is predominantly neutrophilic. When the airways are exposed to cigarette smoke macrophages, CD8+ T cells and epithelial cells are activated and release pro-inflammatory mediators, oxidants, cytokines and neutophilic chemotactic factors, IL-8, GROα, ENA-78 and leukotrienes. IL-8, GROα and ENA-78 are selective chemoattractants for neutrophils. In human neutrophils IL-8 binds two distinct receptors with similar affinity, CXCR1 and CXCR2. Closely related chemokines including GROα, β, γ, NAP-2 and ENA-78 bind only to CXCR2. Inhibiting neutrophil recruitment is therefore a recognised therapeutic strategy for treating several lung diseases. Blocking the binding of IL-8, GROα and ENA-78 to the chemokine receptor CXCR2 can provide beneficial effects in patients with COPD by suppressing the infiltration and activation of key inflammatory cells, thereby reducing subsequent tissue damage, mucus secretion, airflow obstruction and disease progression.

The IL-8 and GROα chemokine inhibitory properties of compounds of the invention can be demonstrated in the following ASSAYS:

Receptor Binding Assay

IL-8 (human recombinant) are obtained from Amersham Pharmacia Biotech, with specific activity 2000 Ci/mmol. All other chemicals are of analytical grade. Human recombinant CXCR2 receptor expressed in Chinese hamster ovary cells (CHO-K1) is purchased from Euroscreen. The Chinese hamster ovary membranes are prepared according to protocol supplied by Euroscreen. Membrane protein concentration is determined using a Bio-Rad protein assay. Assays are performed in a 96-well micro plate format according the method described in White, et al., J Biol. Chem., 1998, 273, 10095). Each reaction mixture contains 0.05 mg/ml CXCR2 membrane protein in 20 mM Bis-Tris-propane, pH 8.0, containing 1.2 mM $MgSO_4$, 0.1 mM EDTA, 25 mM NaCl and 0.03% CHAPS. In addition, compound of interest pre-dissolved in dimethylsulphoxide (DMSO) so as to reach a final concentration of between 10 μM and 0.0005 μM (final concentration of DMSO 2% (v/v)) is added. Binding is initiated by addition of 0.02 nM $^{125}$I-IL-8. After 2 hours at room temperature the plate is harvested using a Brandell™ 96-well harvester onto glass fibre filter plate (GF/c) blocked with 1% polyethyleneimine +0.5% BSA and washed 3 times with 25 mM NaCl, 10 mM TrisHCl, 1 mM $MgSO_4$, 0.5 mM EDTA, 0.03% CHAPS, pH 7.4. The filter is dried at 50° C. overnight. Backseal is applied to the plate and 50 μl of liquid scintillation fluid added. The counts are measured on the Packard Topcount™ scintillation counter.

[$^{35}$S]-GTPγS Binding Assay for Human CXCR2 Receptor Using SPA Technology

[$^{35}$S]-GTPγS (with specific activity 1082 Ci/mmol) and wheat germ agglutinin poly vinyl toluene scintillation proximity beads are purchased from Amersham Pharmacia Biotech. The Chinese hamster ovary cell (CHO-K1) membranes expressing human CXCR2 receptors are purchased from Biosignal Packard Inc. All other chemicals are of analytical grade. White non-binding surface 96 well Optiplate™ microplates are obtained from Packard. Recombinant human IL-8 is synthesised, cloned and expressed in *Escherichia coli* as described previously (Lindley I, et al., Proc. Natl. Acad. Sci., 1988, 85(23):9199). The assay is performed in duplicate in 96 well Optiplate™ microplate in a final volume of 250 μl per well. Compounds are diluted in DMSO (0.5% final concentration) and incubated in 20 mM HEPES buffer pH 7.4 containing 10 mM $MgCl_2$, 100 mM NaCl, 1 mM EDTA plus 100 nM IL-8, 50 μM GDP and 500 μM [$^{35}$S]GTPγS per well. SPA beads (1 mg/well final concentration) were pre-mixed with the membranes (10 μg/well final concentration) in assay buffer: 20 mM HEPES buffer pH 7.4 containing 10 mM $MgCl_2$, 100 mM NaCl, 1 mM EDTA. The bead membrane mixture is added to each well, plates are sealed and incubated at room temperature for 60 minutes. The plate is centrifuged and read on Packard TopCoun™ scintillation counter, program [$^{35}$S dpm] for 1 min/well. Data are expressed as the % response to 100 nM IL-8 minus basal.

Chemotaxis Assay

The in vitro inhibitory properties of these compounds are determined in the neutrophil chemotaxis assay. Assays are performed in a 96-well plate format according to previously published method (Frevert C W, et al., *J Immunolog. Methods,* 1998, 213, 41). 96-well chemotaxis chambers 5 µm are obtained from Neuro Probe, all cell buffers are obtained from Invitrogen Paisley, UK, dextran -T500 and Ficoll-Paque Plus™ density gradient centrifugation media are purchased from Pharmacia Biotech Buckinghamshire, UK. Calcein-AM dye is obtained from Molecular Probes. Neutrophils are isolated as previously described (Haslett, C., et al. *Am J Path.,* 1985, 119:101). Citrated whole blood is mixed with 4% (w/v) dextran-T500 and allowed to stand on ice for 30 minutes to remove erythrocytes. Granulocytes (PMN) are separated from peripheral blood mononuclear cells by layering 15 ml of cell suspension onto 15 ml Ficoll-Paque PLUS density gradient and centrifuged at 250 xg for 25 minutes. Following centrifugation any erythrocytes contamination of PMN pellet is removed by hypotonic shock lysis using 10 ml ice-cold endotoxin-free sterile water for 50 seconds and neutralised with 10 ml of cold 2× phosphate buffered saline. Isolated neutrophils ($1 \times 10^7$) are labelled with the fluorochrome calcein-AM (5 µg) in a total volume of 1 ml and incubated for 30 minutes at 37° C. The labelled cells are washed with RPMI without phenol red +0.1% bovine serum albumin, prior to use the cells are counted and adjusted to a final concentration of $5 \times 10^6$ cells/ml. The labelled neutrophils are then mixed with test compounds (0.001-1000 nM) diluted in DMSO (0.1% final concentration) and incubated for 10 minutes at room temperature. The chemoattractants (29 µl) are placed in the bottom chamber of a 96-well chemotaxis chamber at a concentration between (0.1-5 nM). The polycarbonate filter (5 µm) is overlaid on the plate, and the cells (25 µl) are loaded on the top filter. The cells are allowed to migrate for 90 minutes at 37° C. in a humidified incubator with 5% $CO_2$. At the end of the incubation period, migrated cells are quantified using a multi-well fluorescent plate reader (Fluoroskan II™, Labsystems) at 485 nm excitation and 538 nm emission. Each compound is tested in quadruplet using 4 different donors. Positive control cells, i.e. cells that have not been treated with compound, are added to the bottom well. These represent the maximum chemotactic response of the cells. Negative control cells, i.e. those that have not been stimulated by a chemoattractant, are added to the bottom chamber. The difference between the positive control and negative control represents the chemotactic activity of the cells.

The compounds of the Examples herein below generally have $IC_{50}$ values below 10 µM in the [$^{35}$S]-GPTγS binding assay. For instance, the compounds of Examples 7 and 17 have $IC_{50}$ values of 22 nM and 58 nM, respectively.

Having regard to their inhibition of binding of CXCR2, compounds of the invention are useful in the treatment of conditions or diseases mediated by CXCR2, for example inflammatory or allergic conditions or diseases, particularly chronic obstructive pulmonary airways or lung disease (COPD, COAD or COLD), including chronic bronchitis or dyspnea associated therewith, emphysema, bronchiolitis obliterans syndrome and severe asthma. Compounds of the present invention are further useful in the treatment of various diseases, such as cancer, e.g. ovarian cancer, prostate cancer, melanoma including metastatic melanoma, lung cancer, e.g. non small cell lung cancer, renal cell carcinoma; tumour angiogenesis, ischaemia/reperfusion injury, delayed graft function, osteoarthritis, myeloid metaplasia with myelofibrosis, Adenomyosis, contact hypersensitivity (skin) and in wound healing. Treatment in accordance with the invention may be symptomatic or prophylactic.

Prophylactic efficacy in the treatment of chronic bronchitis or COPD will be evidenced by reduced frequency or severity, will provide symptomatic relief and reduce disease progression, improvement in lung function. It may further be evidenced by reduced requirement for other, symptomatic therapy, i.e. therapy for or intended to restrict or abort symptomatic attack when it occurs, for example anti-inflammatory (e.g. corticosteroid) or bronchodilatory.

Other inflammatory or obstructive airways diseases and conditions to which the invention is applicable include acute lung injury (ALI), acute/adult respiratory distress syndrome (ARDS), idiopathic pulmonary fibrosis, fibroid lung, airway hyperresponsiveness, dyspnea, pulmonary fibrosis, allergic airway inflammation, small airway disease, lung carcinoma, acute chest syndrome in patients with sickle cell disease and pulmonary hypertension, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Compounds of the invention are also useful for treating respiratory viral infections, which exacerbate underlying chronic conditions such as asthma, chronic bronchitis, COPD, otitis media, and sinusitis. The respiratory viral infection treated may be associated with secondary bacterial infection, such as otitis media, sinusitis or pneumonia.

Compounds of the invention are also useful in the treatment of inflammatory conditions of the skin, for example psoriasis, atopic dermatitis, lupus erythematosus, and other inflammatory or allergic conditions of the skin.

Compounds of the invention may also be used for the treatment of other diseases or conditions, in particular diseases or conditions having an inflammatory component, for example, diseases affecting the nose including allergic rhinitis, e.g. atrophic, chronic, or seasonal rhinitis, inflammatory conditions of the gastrointestinal tract, for example inflammatory bowel disease such as ulcerative colitis and Crohn's disease, diseases of the bone and joints including rheumatoid arthritis, psoriatic arthritis, and other diseases such as atherosclerosis, multiple sclerosis, and acute and chronic allograft rejection, e.g. following transplantation of heart, kidney, liver, lung or bone marrow.

Compounds of the invention are also useful in the treatment of endotoxic shock, glomerulonephritis, cerebral and cardiac ischemia, Alzheimer's disease, cystic fibrosis, virus infections and the exacerbations associated with them, acquired immune deficiency syndrome (AIDS), multiple sclerosis (MS), *Helicobacter pylori* associated gastritis, and cancers, particularly the growth of ovarian cancer.

Compounds of the invention are also useful for treating symptoms caused by viral infection in a human which is caused by the human rhinovirus, other enterovirus, coronavirus, herpes viruses, influenza virus, parainfluenza virus, respiratory syncytial virus or an adenovirus. Compounds of the invention are also useful for treating pancreatitis.

The effectiveness of a compound of the invention in inhibiting inflammatory conditions, for example in inflammatory airways diseases, may be demonstrated in an animal model, e.g. mouse, rat or rabbit model, of airway inflammation or other inflammatory conditions, for example as described by Wada et al, *J. Exp. Med.* (1994) 180:1135-40; Sekido et al, *Nature* (1993) 365:654-57; Modelska et al., *Am. J. Respir. Crit. Care. Med.* (1999) 160:1450-56; and Laffon et al (1999) *Am. J. Respir. Crit. Care Med.* 160:1443-49.

The compounds of the invention are also useful as co-therapeutic compounds for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422, WO 04/05285, WO2004096800, WO2006048225 and WO2008025541; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially a compound of formula

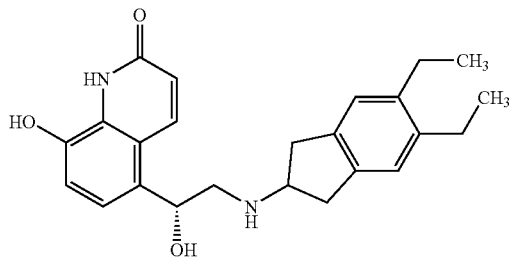

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 and WO 04/80964.

Such antihistamine drug substances include cetirizine hydrochloride, acetaminophen, clemastine fumarate, promethazine, loratidine, desloratidine, diphenhydramine and fexofenadine hydrochloride.

Combinations of compounds of the invention and anticholinergic or antimuscarinic compounds, steroids, beta-2 agonists, PDE4 inhibitors, dopamine receptor agonists, LTD4 antagonists or LTB4 antagonists may also be used. Other useful combinations of compounds of the invention with anti-inflammatory drugs are those with other antagonists of chemokine receptors, e.g. CCR-1, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]-tetrahydro-N,N-dimethyl-2H-pyran-4-aminium chloride (TAK-770), CCR-5 antagonists described in U.S. Pat. No. 6,166,037 (particularly claims 18 and 19), WO 0066558 (particularly claim 8), and WO 0066559 (particularly claim 9).

In accordance with the foregoing, the invention also provides a method for the treatment of a condition or disease mediated by CXCR2, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition or disease mediated by CXCR2, for example an inflammatory or allergic condition or disease, particularly an inflammatory or obstructive airways disease.

The compounds of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic compound such as an anti-inflammatory bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture, e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) a compound of the invention in inhalable form, e.g. in an aerosol or other atomisable composition or in inhalable particulate, e.g. micronised form, (B) an inhalable medicament comprising a compound of the invention in inhalable form; (C) a pharmaceutical product comprising such a compound of the invention in inhalable form in association with an inhalation device; and (D) an inhalation device containing a compound of the invention in inhalable form.

Dosages of compounds of the invention employed in practising the present invention will of course vary depending, for example, on the particular condition to be treated, the effect desired and the mode of administration. In general, suitable daily dosages for administration by inhalation are of the order of 0.01 to 1 mg/kg per day while for oral administration suitable daily doses are of the order of 0.005 to 100 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily.

In the following examples all temperatures are in degree (°) Celsius.

The following ABBREVIATIONS are used:
Et$_3$N triethylamine
EtOAc ethyl acetate
Et$_2$O diethyl ether,
EtOH ethanol
HMDS hexamethyldisilazane
MeOH methanol
MeCN acetonitrile
Na$_2$SO$_4$ sodium sulfate
TBME tert-butyl methyl ether
THF tetrahydrofuran
rt room temperature

EXAMPLES

Example 1

3-{3,4-Dioxo-2-[(tetrahydrofuran-2-ylmethyl)-amino]-cyclobut-1-enylamino}-2-hydroxy-N,N-dimethyl-benzamide 100 mg of 3-(2-Ethoxy-3,4-dioxo-cyclobut-1-enylamino)-2-hydroxy-N,N-dimethyl-benzamide (Intermediate A) are added under an inert atmosphere of argon to a solution of 66 mg of 2-(aminomethyl)tetrahydrofuran in 1 ml of dry MeOH. A reaction mixture obtained is stirred at rt for 2 hours, solvent is evaporated and a residue obtained is purified by flash chromatography on silica eluting with EtOAc:MeOH (95:5) followed by trituration with Et$_2$O.

The title compound is obtained. MH$^+$ 360.

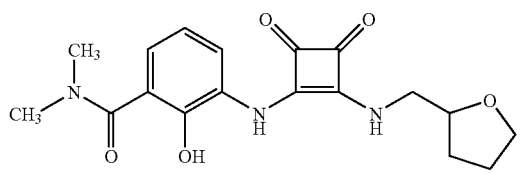

Example 2

2-Hydroxy-N,N-dimethyl-3-{2-[(R)-1-(5-methyl-tetrahydrofuran-2-yl)-propylamino]-3,4-dioxo-cyclobut-1-enylamino}-benzamide To a solution of 676 mg of 3-(2-Ethoxy-3,4-dioxo-cyclobut-1-enylamino)-2-hydroxy-N,N-dimethyl-benzamide (Intermediate A) and 1.4 g of (R)-1-(5-methyl-tetrahydrofuran-2-yl)-propylamine para-toluenesulfonate salt (Intermediate B) in 10 ml of dry MeCN, 0.62 ml of Et$_3$N are added under an inert atmosphere of argon. A reaction mixture obtained is stirred overnight at rt, solvent is evaporated and a residue obtained is purified by flash chromatography on silica eluting with EtOAc followed by trituration with Et$_2$O.

The title compound is obtained. MH$^+$ 402

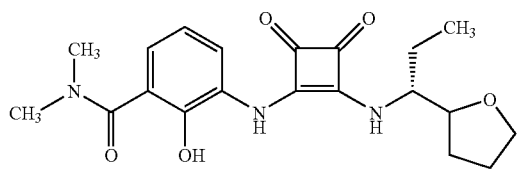

Example 3

6-Chloro-2-hydroxy-N,N-dimethyl-3-{2-[(R)-1-((2R,5R)-5-methyl-tetrahydrofuran-2-yl)-propylamino]-3,4-dioxo-cyclobut-1-enylamino}-benzenesulfonamide a.) 2-tert-Butyl-6-chloro-benzooxazole-7-sulfonic acid dimethylamide

To an ice-cooled solution of 3.0 g of 2-tert-butyl-6-chloro-benzooxazole-7-sulfonyl chloride (US 2007/0249672 page 9) in 8 ml of dry THF, 1.19 ml of Et$_3$N followed by 1.85 ml of 40% dimethylamine in H$_2$O are added under an inert atmosphere of nitrogen. A mixture obtained is allowed to warm to it and is added to 100 ml of H$_2$O. A mixture obtained is extracted with 150 ml EtOAc and an organic portion obtained is washed with 100 ml of H$_2$O. The two layers are partitioned using a small amount of MeOH and an organic extract obtained is dried and solvent is evaporated.

The title compound is obtained. MH$^+$ 317.

b.) 3-Amino-6-chloro-2-hydroxy-N,N-dimethyl-benzenesulfonamide

A stirred suspension of 1.12 g of 2-tert-butyl-6-chloro-benzooxazole-7-sulfonic acid dimethylamide in 5 ml of dioxane is treated with 1.3 ml of conc. H$_2$SO$_4$ followed by 1.3 ml of H$_2$O at rt under an inert atmosphere of nitrogen. A reaction mixture obtained is heated at reflux for 4 hours and stirred at rt overnight. Solvent is evaporated and a residue obtained is dissolved in 100 ml of EtOAc. A solution obtained is basified to pH 14 using 2M NaOH and 250 ml of H$_2$O and 150 ml of EtOAc are added. An organic portion obtained is separated and an aqueous portion obtained is extracted with 2×EtOAc. The combined organic extracts obtained are dried and solvent is evaporated.

The title compound is obtained. MH$^+$ 251.

c.) 6-Chloro-3-(2-ethoxy-3,4-dioxo-cyclobut-1-enylamino)-2-hydroxy-N,N-dimethyl-benzenesulfonamide To a stirred solution of 393 mg of 3,4-diethoxy-3-cyclobutene-1,2-dione in 10 ml of dry EtOH are added 579 mg of 3-amino-6-chloro-2-hydroxy-N,N-dimethyl-benzene sulfonamide followed by 188 µl of Et$_3$N at rt under an inert atmosphere of nitrogen. After stirring at rt over 3 days, solvent is evaporated and a residue obtained is purified by flash chromatography on silica eluting with 20-50% EtOAc in iso-hexane.

The title compound is obtained. MH$^+$ 375.

d.) 6-Chloro-2-hydroxy-N,N-dimethyl-3-{2-[(R)-1-((2R,5R)-5-methyl-tetrahydrofuran-2-yl)-propylamino]-3,4-dioxo-cyclobut-1-enylamino}-benzenesulfonamide To a stirred solution of 253 mg of 6-chloro-3-(2-ethoxy-3,4-dioxo-cyclobut-1-enylamino)-2-hydroxy-N,N-dimethyl-benzenesulfonamide in 5 ml of dry MeCN are added 362 mg of (R)-1-((2R,5R)-5-methyl-tetrahydrofuran-2-yl)-propylamine p-toluenesulfonate salt followed by 94 µl of Et$_3$N at rt under an inert atmosphere of nitrogen. A reaction mixture obtained is heated at reflux for 45 minutes and solvent is evaporatedA residue obtained is purified by flash chromatography on silica eluting with 30-40% EtOAc in iso-hexane. The title compound is obtained. MH$^+$ 472.

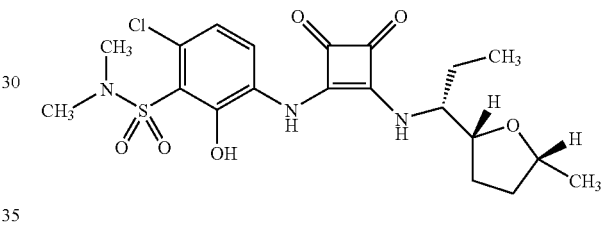

Example 4 to 8 are prepared in an analagous way to Example 1 using the appropriately substituted benzamide or benzenesulfonamide and amines. The benzenesulfonamides are prepared analogously to 6-chloro-3-(2-ethoxy-3,4-dioxo-cyclobut-1-enylamino)-2-hydroxy-N,N-dimethyl-benzenesulfonamide (Ex. 3 step 3) using the appropriate amine in Ex. 3 step 1.

| Ex. | Structure | Name | MH$^+$ |
|---|---|---|---|
| 4 | ![structure] | 3-[3,4-Dioxo-2-(tetrahydrothiophen-3-ylamino)-cyclobut-1-enylamino]-2-hydroxy-N,N-dimethyl-benzamide | 362 |
| 5 | ![structure] | 6-Chloro-3-[3,4-dioxo-2-(tetrahydrothiophen-3-ylamino)-cyclobut-1-enylamino]-2-hydroxy-N,N-dimethyl-benzenesulfonamide | 432 |

-continued

| Ex. | Structure | Name | MH+ |
|---|---|---|---|
| 6 | 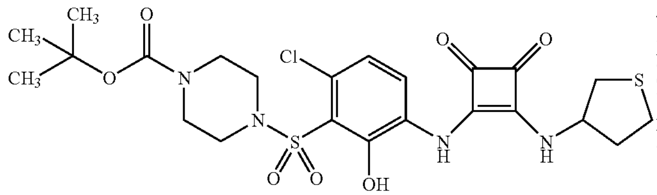 | 4-(6-Chloro-3-[3,4-dioxo-2-(tetrahydrothiophen-3-ylamino)-cyclobut-1-enylamino]-2-hydroxy-benzenesulfonyl]-piperazine-1-carboxylic acid tert-butyl ester | 574 |
| 7 | 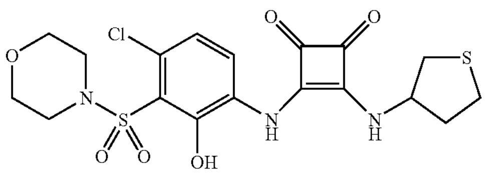 | 3-[4-Chloro-2-hydroxy-3-(morpholine-4-sulfonyl)-phenylamino]-4-(tetra-hydro-thiophen-3-ylamino)-cyclobut-3-ene-1,2-dione | 475 |
| 8 | 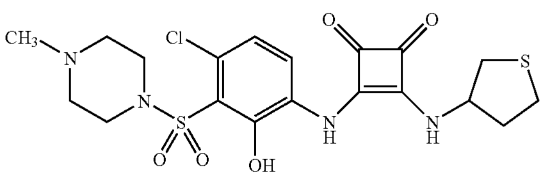 | 3-[4-Chloro-2-hydroxy-3-(4-methyl-piperazine-1-sulfonyl)-phenylamino]-4-(tetrahydrothiophen-3-ylamino)-cyclobut-3-ene-1,2-dione | 488 |

Example 9

3-(4-Chloro-2-hydroxy-phenylamino)-4-(tetrahydrothiophen-3-ylamino)-cyclobut-3-ene-1,2-dione A solution of 170 mg of 3,4-diethoxy-cyclobut-3-ene-1,2-dione in 10 ml of EtOH is treated with 0.17 ml of TEA followed by 144 mg of 2-amino-5-chlorophenol and shaken at rt overnight. To the mixture obtained are added 103 mg of 2-amino-tetrahydrothiophene and shaking is continued for a further 4 hours at rt. A suspension obtained is filtered and a solid obtained is dried. The title compound is obtained. MH+ 327

Example 10

3-{3,4-Dioxo-2-[((R)-5-oxo-tetrahydrofuran-2-ylmethyl)-amino]-cyclobut-1-enylamino}-2-hydroxy-N,N-dimethyl-benzamide This compound is prepared in an analagous way to Example 1 using the appropriately substituted benzamide and amines.

Example 11 to 13 are prepared in an analagous way to Example 2 by replacing (R)-1-(5-methyl-tetrahydrofuran-2-yl)-propylamine, para-toluenesulfonate salt (Intermediate B) with the appropriate amine.

| Ex. | Structure | Name | MH+ |
|---|---|---|---|
| 11 | 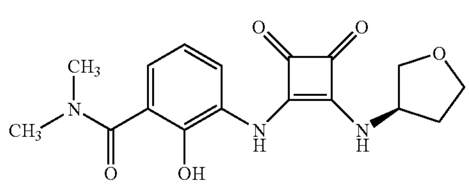 | 3-{3,4-Dioxo-2-[(R)-(tetrahydrofuran-3-yl)amino]-cyclobut-1-enylamino)-2-hydroxy-N,N-dimethyl-benzamide | 346 |

| Ex. | Structure | Name | MH+ |
|---|---|---|---|
| 12 | 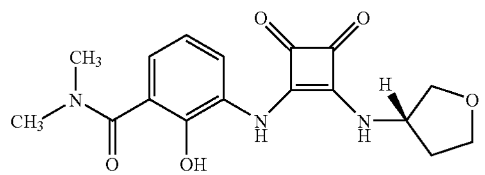 | 3-{3,4-Dioxo-2-[(S)-(tetrahydrofuran-3-yl)amino]-cyclobut-1-enylamino}-2-hydroxy-N,N-dimethyl-benzamide | 346 |
| 13 | 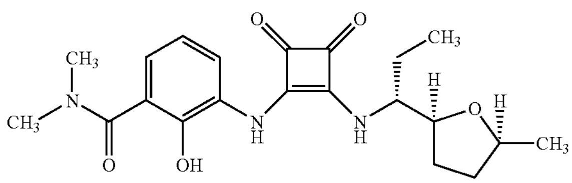 | 2-Hydroxy-N,N-dimethyl-3-{2-[(R)-1-((2S,5S)-5-methyl-tetrahydrofuran-2-yl)-propylamino]-3,4-dioxo-cyclobut-1-enylamino)-benzamide | 402 |

Example 14 to 23 are prepared in an analagous way to Example 3 using the appropriately substituted benzenesulfonamide and amines. The benzenesulfonamides are prepared analogously to 6-chloro-3-(2-ethoxy-3,4-dioxo-cyclobut-1-enylamino)-2-hydroxy-N,N-dimethyl-benzenesulfonamide (Ex. 3 step 3) using the appropriate amine in Ex. 3 step 1.

| Ex. | Structure | Name | MH+ |
|---|---|---|---|
| 14 | 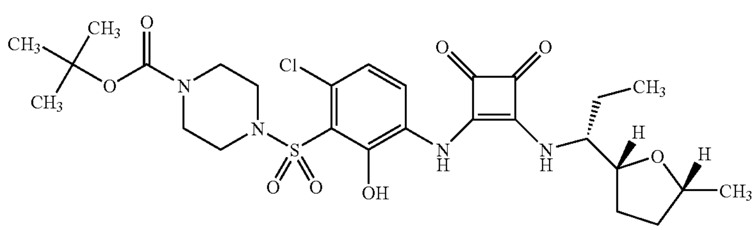 | 4-(6-Chloro-2-hydroxy-3-{2-[(R)-1-((2R,5R)-5-methyl-tetrahydrofuran-2-yl)-propylamino]-3,4-dioxo-cyclobut-1-enylamino}-benzene sulfonyl)-piperazine-1-carboxylic acid tert-butyl ester | 613.5 |
| 15 | 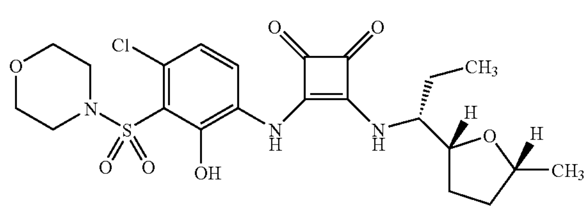 | 3-[4-Chloro-2-hydroxy-3-(morpholine-4-sulfonyl)-phenylamino]-4-[(R)-1-((2R,5R)-5-methyl-tetrahydrofuran-2-yl)-propylamino]-cyclobut-3-ene-1,2-dione | 514 |
| 16 | 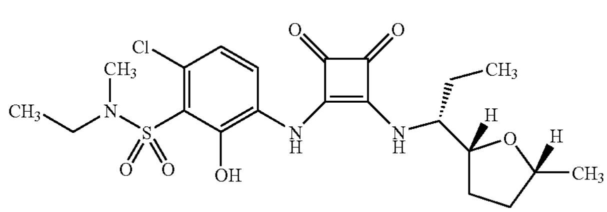 | 6-Chloro-N-ethyl-2-hydroxy-N-methyl-3-{2-[(R)-1-((2R,5R)-5-methyl-tetrahydrofuran-2-yl)-propylamino]-3,4-dioxo-cyclobut-1-enylamino}-benzene-sulfonamide | 486 |
| 17 | 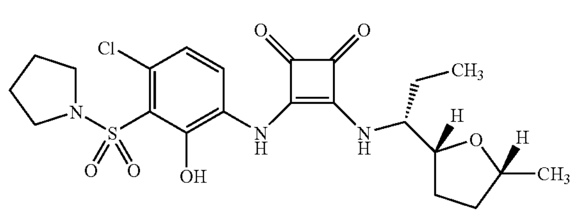 | 3-[4-Chloro-2-hydroxy-3-(pyrrolidine-1-sulfonyl)-phenylamino]-4-[(R)-1-((2R,5R)-5-methyl-tetrahydrofuran-2-yl)-propylamino]-cyclobut-3-ene-1,2-dione | 498 |

-continued

| Ex. | Structure | Name | MH⁺ |
|---|---|---|---|
| 18 | 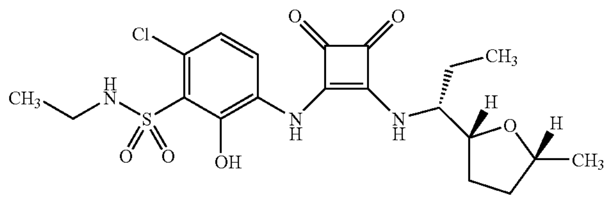 | 6-Chloro-N-ethyl-2-hydroxy-3-{2-[(R)-1-((2R,5R)-5-methyl-tetrahydrofuran-2-yl)-propylamino]-3,4-dioxo-cyclobut-1-enylamino}benzenesulfonamide | 472 |
| 19 | 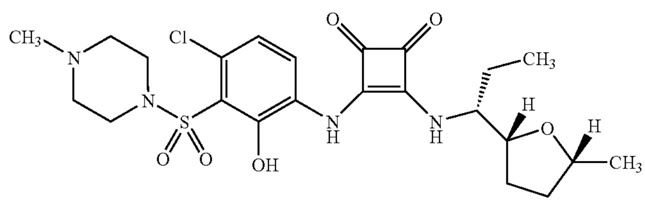 | 3-[4-Chloro-2-hydroxy-3-(4-methyl-piperazine-1-sulfonyl)-phenylamino]4-[(R)-1-((2R,5R)-5-methyl-tetrahydrofuran-2-yl)-propylamino]-cyclobut-3-ene-1,2-dione | 528 |
| 20 | 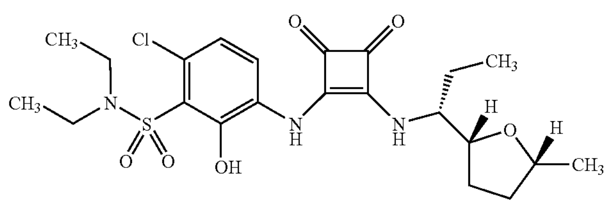 | 6-Chloro-N,N-diethyl-2-hydroxy-3-{2-[(R)-1-((2R,5R)-5-methyl-tetrahydrofuran-2-yl)-propylamino]-3,4-dioxo-cyclobut-1-enylamino}-benzenesulfonamide | 500 |
| 21 | 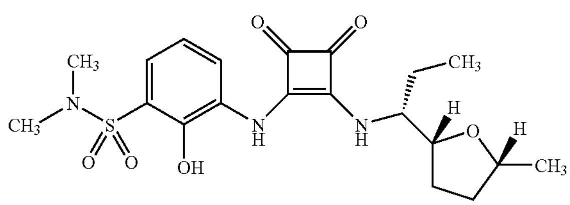 | 2-Hydroxy-N,N-dimethyl-3-{2-[(R)-1-((2R,5R)-5-methyl-tetrahydrofuran-2-yl)-propylamino]-3,4-dioxo-cyclobut-1-enylamino)-benzene sulfonamide | 438 |
| 22 | 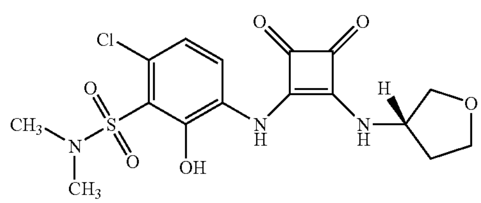 | 6-Chloro-3-{3,4-dioxo-2-[(S)-(tetrahydrofuran-3-yl)amino]-cyclobut-1-enylamino}-2-hydroxy-N,N-dimethyt-benzene sulfonamide | 416 |
| 23 | 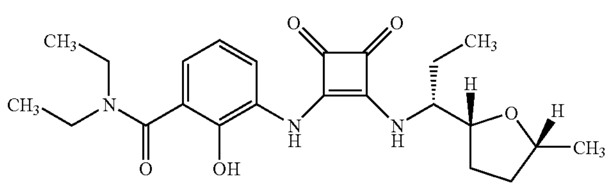 | N,N-Diethyl-2-hydroxy-3-{2-[(R)-1-((2R,5R)-5-methyl-tetrahydrofuran 2-yl)-propylamino]-3,4-dioxo-cyclobut-1-enylamino}-benzamide | 430 |

Example 24

3-(4-Chloro-2-hydroxy-3-methanesulfonyl-phenylamino)-4-(tetrahydrothiophen-3-ylamino)-cyclobut-3-ene-1,2-dione a.) 2-tert-Butyl-6-chloro-7-methanesulfonyl-benzooxazole A solution of 204 mg of Na₂SO₃ and 409 mg of NaHCO₃ in 4 ml H₂O is heated to 75° and treated portionwise with 0.5 g of 2-tert-butyl-6-chloro-benzooxazole-7-sulfonyl chloride (US 2007/0249672 page 9). A mixture obtained is heated at 75° for 2 hours and 4 ml of EtOH are added followed by 0.11 ml of iodomethane. A mixture obtained is heated at 90° overnight and allowed to cool to rt. A mixture obtained is extracted with 3×30 ml of EtOAc and the combined organic extracts obtained are washed with brine, dried over MgSO₄ and solvent is evaporated. The title compound is obtained.

b.) 3-(4-Chloro-2-hydroxy-3-methanesulfonyl-phenylamino)-4-ethoxy-cyclobut-3-ene-1,2-dione The title compound is prepared analogously to 6-chloro-3-(2-ethoxy-3,4-dioxo-cyclobut-1-enylamino)-2-hydroxy-N,N-dimethyl-benzenesulfonamide (Ex. 3 step 2) by replacing 2-tert-butyl-6-chloro-benzooxazole-7-sulfonic acid dimethylamide (Ex. 3 step 2) with 2-tert-Butyl-6-chloro-7-methanesulfonyl-benzooxazole.

c.) 3-(4-Chloro-2-hydroxy-3-methanesulfonyl-phenylamino)-4-(tetrahydrothiophen-3-ylamino)-cyclobut-3-ene-1,2-dione The title compound is prepared from 3-(4-chloro-2-hydroxy-3-methanesulfonyl-phenylamino)-4-ethoxy-cyclobut-3-ene-1,2-dione analogously to 6-chloro-2-hydroxy-N,N-dimethyl-3-{2-[(R)-1-((2R,5R)-5-methyl-tetrahydrofuran-2-yl)-propylamino]-3,4-dioxo-cyclobut-1-enylamino}-benzenesulfonamide (Example 3) by replacing (R)-1-((2R,5R)-5-methyl-tetrahydrofuran-2-yl)-propylamine p-toluenesulfonate salt with tetrahydrothiophen-3-ylamine. The reaction is carried out in EtOH. The title compound is obtained. MH+ 403.

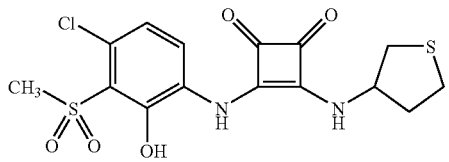

Example 25

3-(4-Chloro-2-hydroxy-3-methanesulfonyl-phenylamino)-4-[(R)-1-((2R,5R)-5-methyl-tetrahydrofuran-2-yl)-propylamino]-cyclobut-3-ene-1,2-dione The title compound is prepared analogously to Example 26 by replacing tetrahydrothiophen-3-ylamine with (R)-1-((2R,5R)-5-methyl-tetrahydrofuran-2-yl)-propylamine p-toluenesulfonate salt. MH+ 443

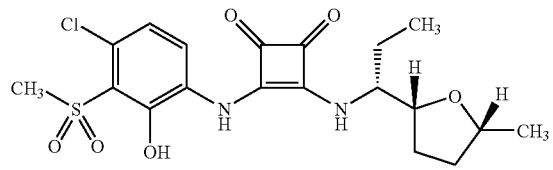

Example 26

3-[4-Chloro-2-hydroxy-3-(piperazine-1-sulfonyl)-phenylamino]-4-[(R)-1-((2R,5R)-5-methyl-tetrahydrofuran-2-yl)-propylamino]-cyclobut-3-ene-1,2-dione 0.4 ml of TFA are added dropwise to an ice-cooled solution of 54 mg of 4-(6-chloro-2-hydroxy-3-{2-[(R)-1-((2R,5R)-5-methyl-tetrahydrofuran-2-yl)-propylamino]-3,4-dioxo-cyclobut-1-enylamino}-benzene sulfonyl)-piperazine-1-carboxylic acid tert-butyl ester (Ex. 17) in 1 ml of dry DCM under an inert atmosphere of nitrogen. After stirring at rt for 4 hours, a reaction mixture obtained is diluted with 25 ml DCM and 25 ml NaHCO$_{3(aq)}$ are added. An organic portion is separated and washed with 3×NaHCO$_{3(aq)}$, dried over MgSO$_4$ and solvent is evaporated. The title compound is obtained. MH+ 513.

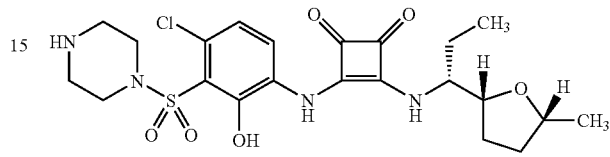

Example 27

3-Chloro-2-(piperazine-1-sulfonyl)-6-(tetrahydrothiophen-3-ylamino)-phenol

The title compound is prepared from 4-{6-chloro-3-[3,4-dioxo-2-(tetrahydrothiophen-3-ylamino)-cyclobut-1-enylamino]-2-hydroxy-benzenesulfonyl}-piperazine-1-carboxylic acid tert-butyl ester (Example 8) analogously to Example 30. MH+ 473.

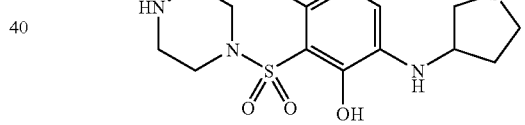

Example 28 to 37 are prepared in an analagous way to Example 3 using the appropriately substituted benzenesulfonamide and amines. The benzenesulfonamides are prepared analogously to 6-chloro-3-(2-ethoxy-3,4-dioxo-cyclobut-1-enylamino)-2-hydroxy-N,N-dimethyl-benzenesulfonamide (Ex. 3 step 3) using the appropriate amine in Ex. 3 step 1.

| Ex. | Structure | Name | MH+ |
|---|---|---|---|
| 28 | 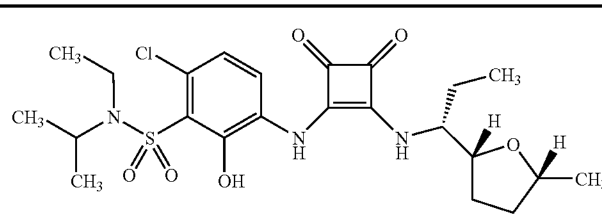 | 6-Chloro-N-ethyl-2-hydroxy-N-isopropyl-3-{2-[(R)-1-((2R,5R)-5-methyl-tetrahydrofuran-2-yl)-propylamino]-3,4-dioxo-cyclobut-1-enylamino}-benzenesulfonamide | 514 |

| Ex. | Structure | Name | MH+ |
|---|---|---|---|
| 29 | 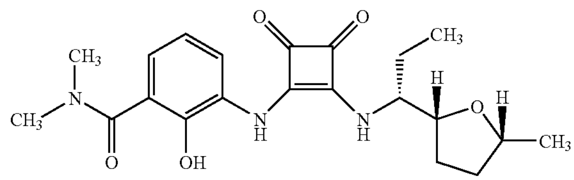 | 2-Hydroxy-N,N-dimethyl-3-{2-[(R)-1-((2R,5R)-5-methyl-tetrahydrofuran-2-yl)-propylamino]-3,4-dioxo-cyclobut-1-enylamino}-benzamide | 402 |
| 30 | 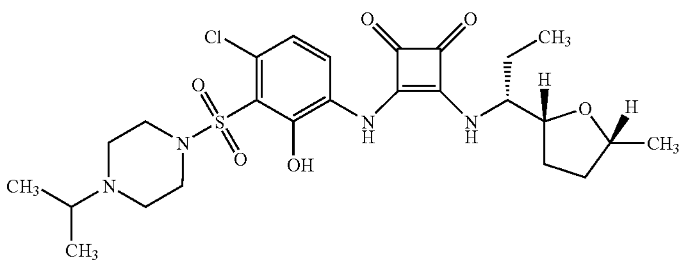 | 3-[4-Chloro-2-hydroxy-3-(4-propyl-piperazine-1-sulfonyl)-phenylamino]-4-[(R)-1-((2R,5R)-5-methyl-tetrahydrofuran-2-yl)-propylamino]-cyclobut-3-ene-1,2-dione | 555 |
| 31 | 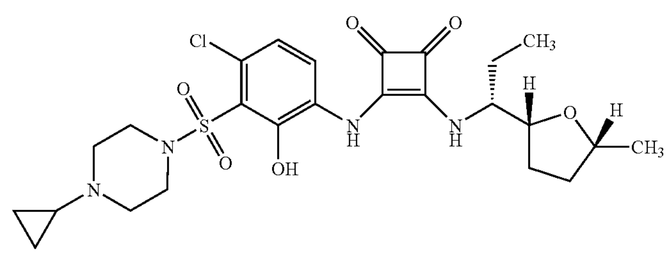 | 3-[4-Chloro-3-(4-cyclopropyl-piperazine-1-sulfonyl)-2-hydroxy-phenylamino]-4-[(R)-1-((2R,5R)-5-methyl-tetrahydrofuran-2-yl)-propylamino)-cyclobut-3-ene-1,2-dione | 553 |
| 32 | 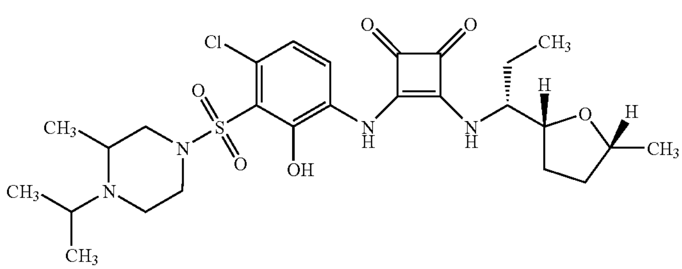 | 3-[4-Chloro-2-hydroxy-3-(4-isopropyl-3-methyl-piperazine-1-sulfonyl)-phenylamino]-4-[(R)-1-((2R,5R)-5-methyl-tetrahydrofuran-2-yl)-propylamino]-cyclobut-3-ene-1,2-dione | 569 |
| 33 | 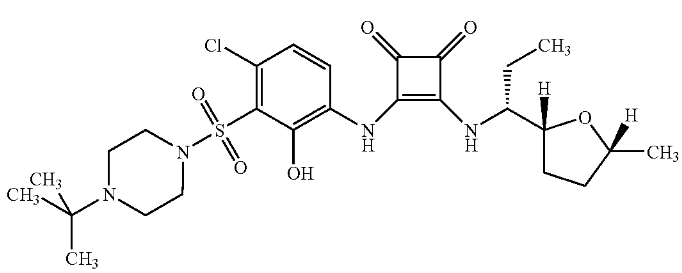 | 3-[3-(4-tert-Butyl-piperazine-1-sulfonyl)-4-chloro-2-hydroxy-phenylamino]-4-[(R)-1-((2R,5R)-5-methyl-tetrahydrofuran-2-yl)-propylamino)-cyclobut-3-ene-1,2-dione | 569 |
| 34 | 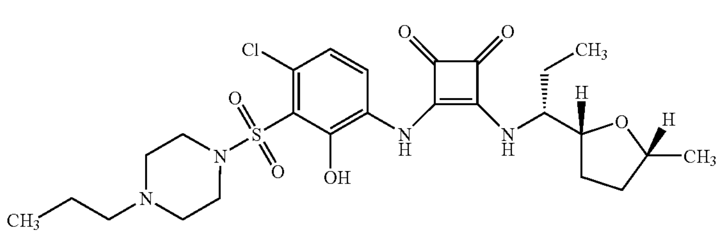 | 3-[4-Chloro-2-hydroxy-3-(4-propyl-piperazine-1-sulfonyl)-phenylamino]-4-[(R)-1-((2R,5R)-5-methyl-tetrahydrofuran-2-yl)-propylamino]-cyclobut-3-ene-1,2-dione | 555 |

| Ex. | Structure | Name | MH+ |
|---|---|---|---|
| 35 | 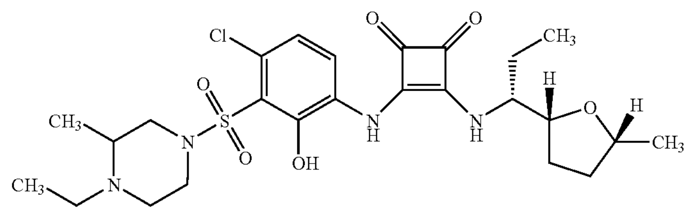 | 3-[4-Chloro-3-(4-ethyl-3-methyl-piperazine-1-sulfonyl)-2-hydroxy-phenyl-amino]-4-[(R)-1-((2R,5R)-5-methyl-tetrahydrofuran-2-yl)-propylamino]-cyclobut-3-ene-1,2-dione | 555 |
| 36 | 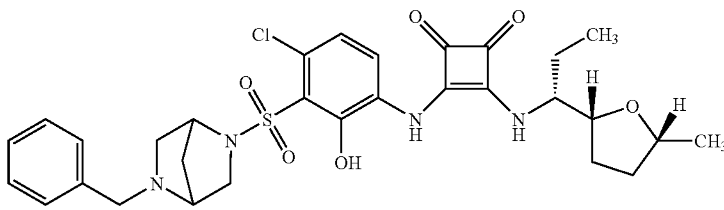 | 3-[3-(5-Benzy-2,5-diaza-bicyclo[2.2.1]heptane-2-sulfonyl)-4-chloro-2-hydroxy-phenylamino]4-[(R)-1-((2R,5R)-5-methyl-tetrahydrofuran-2-yl)-propylamino]-cyclobut-3-ene-1,2-dione | 615 |
| 37 | 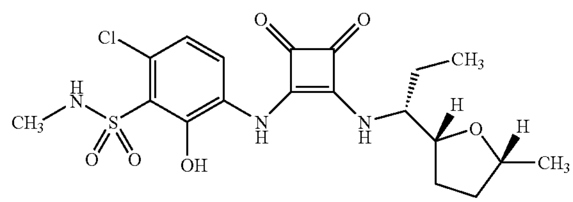 | 6-Chloro-2-hydroxy-N-methyl-3-[2-[(R)-1-((2R,5R)-5-methyl-tetrahydrofuran-2-yl)-propylamino]-3,4-dioxo-cyclobut-1-enylamino)-benzenesulfonamide | 458 |

Example 38

2-Hydroxy-N,N-dimethyl-3-{2-[(R)-1-((2R,5S)-5-methyl-tetrahydrofuran-2-yl)-propylamino]-3,4-dioxo-cyclobut-1-enylamino}-benzamide This compound is isolated from a diastereomeric mixture of 2-hydroxy-N,N-dimethyl-3-{2-[(R)-1-(5-methyl-tetrahydrofuran-2-yl)-propylamino]-3,4-dioxo-cyclobut-1-enylamino}-benzamide (Example 1) using reverse phase mass directed HPLC Column HICHROM HIRPB: 250×20 mm, 10 μm, eluent: 5-20% MeCN/H$_2$O-0.1% diethylamine.

Preparation of Intermediates

Intermediate A

3-(2-Ethoxy-3,4-dioxo-cyclobut-1-enylamino)-2-hydroxy-N,N-dimethyl-benzamide a.) 2-Hydroxy-N,N-dimethyl-3-nitro-benzamide 65 g of 2-nitrosalicylic acid are dissolved in 650 ml of MeCN and 39 ml of thionylchloride are added. A reaction mixture obtained is stirred for 3 hours at 70°. A reaction mixture obtained is cooled to 5° and 700 ml of dimethylamine in THF are added dropwise. A reaction mixture obtained is heated slowly to 35° and stirred for 30 minutes. A reaction mixture obtained is acidified to pH 2 with 1M sulphuric acid and extracted 2× with 500 ml of EtOAc. The organic layers obtained are washed with 300 ml of H$_2$O, dried, filtered, solvent is evaporated and the title compound is obtained.

b.) 3-(2-Ethoxy-3,4-dioxocyclobut-1-enylamino)-2-hydroxy-N,N-dimethyl-benzamide 67.5 g of 2-Hydroxy-N,N-dimethyl-3-nitro-benzamide are dissolved in 1000 ml of EtOH/AcOH 9/1 and degassed 4× by evacuating and purging with argon. 7.5 g of Ru/C are added and the mixture obtained is degassed 4× by evacuating and purging with argon. A reaction mixture obtained is heated to reflux and 25 ml of hydrazine hydrate are added slowly. At 1 hour intervals 3 further portions of 25 ml of hydrazine hydrate are added. A reaction mixture obtained is cooled to rt, filtered and washed with EtOH. Solvent from the filtrate obtained is evaporated. Toluene is added 4× to the residue obtained and solvent is evaporated. A residue obtained is taken up in 1 l of H$_2$O and 1 l of EtOAc. An aqueous layer obtained is extracted 3× with EtOAc. The organic layers obtained are washed 2× with brine, dried, filtered and solvent is evaporated. A residue obtained is purified by column chromatography over 500 g of silica using EtOAc/heptane 1/1 as the eluant to give 3-amino-2-hydroxy-N,N-dimethyl-benzamide.

44 g of 3-amino-2-hydroxy-N,N-dimethyl-benzamide are dissolved in 880 ml of EtOH. 46 g of 3,4-diethoxy-3-cyclobuten-1,2-dione and 4.4 g of K$_2$CO$_3$ are added and the reaction mixture obtained is stirred overnight at rt. Solvent is evaporated. A residue obtained is purified by column chromatography over 500 g of silica using CH$_2$Cl$_2$/MeOH 98/2 as eluent. The product-containing fractions are combined and solvent is evaporated. A residue obtained is suspended in 1 l of MeOH and filtered. This process is repeated a further 3 times. The title compound is obtained.

Intermediate B

(R)-1-(5-Methyl-tetrahydrofuran-2-yl)-propylamine p-toluenesulfonate a.) (R)-2-{[1-(5-Methyl-furan-2-yl)-meth-(E)-ylidene]-amino}-2-phenyl-ethanol 73.8 ml of 5-Methylfuran-2-carbaldehyde are added to 100 g of (R)-2-amino-2-phenyl-ethanol dissolved in 800 ml of THF. A reaction mixture obtained is heated at reflux for 5.5 hours and after cooling to rt solvent is evaporate. The title compound is obtained.

b.) [1-(5-Methyl-furan-2-yl)-meth-(E)-ylidene]-((R)-1-phenyl-2-trimethylsilanyloxy-ethyl)-amine To 179.08 g of (R)-2-{[1-(5-Methyl-furan-2-yl)-meth-(E)-ylidene]-amino}-2-phenyl-ethanol in 1790 ml of THF, 9.9 g of $(NH_4)_2SO_4$ are added followed by the dropwise addition of 70 ml of HMDS and the reaction mixture obtained is heated at reflux overnight. After cooling to rt solvent is evaporated and the catalyst is removed by filtration.
The title compound is obtained.

c.) [(R)-1-(5-Methyl-furan-2-yl)-propyl]-((R)-1-phenyl-2-trimethylsilanyloxy-ethyl)-amine 580 ml of ethylmagnesium bromide as a solution in $Et_2O$ are added dropwise over a period of 30 minutes at 22-35° to a solution of 218 g of [1-(5-methylfuran-2-yl)-meth-(E)-ylidene]-((R)-1-phenyl-2-trimethylsilanyloxy-ethyl)-amine in 100 ml of $Et_2O$. The reaction mixture obtained is cooled to rt and 500 ml of a saturated $NH_4Cl$ solution are added slowly. The reaction mixture obtained is diluted with 1 l of $H_2O$ and extracted with $Et_2O$ (3×200 ml), the organic portions are combined, dried over $Na_2SO_4$, filtered and solvent is evaporated.
The title compound is obtained.

d.) (R)-2-[(R)-1-(5-Methyl-furan-2-yl)-propylamino]-2-phenyl-ethanol 700 ml of 5M $H_2SO_4$ are cooled to 5° and 232 g of [(R)-1-(5-Methyl-furan-2-yl)-propyl]-((R)-1-phenyl-2-trimethylsilanyloxy-ethyl)-amine dissolved in 1 l of TBME are added dropwise over a period of 30 minutes at 5-10°. 345 ml of sec-BuOH and 345 ml of $H_2O$ are added and the reaction mixture obtained is slowly warmed to rt. The aqueous layer obtained is separated. The organic portion obtained is adjusted to pH 11 with 2.5M $NH_4OH$, the aqueous layer is separated and the organic phases obtained are washed 2× with brine. The aqueous layer obtained are back-extracted with 1 l of EtOAc, the organic portions obtained are combined, dried over $Na_2SO_4$, filtered and solvent is evaporated. A residue obtained is dissolved in 500 ml of TBME and 500 ml of $H_2O$ and the pH is adjusted to pH 11 with 2.5M NaOH and extracted 2× with 6 l of TBME. The organic portion obtained is dried, filtered and solvent is evaporated. The title compound is obtained.

e.) (R)-1-(5-Methyl-furan-2-yl)-propylamine, para-toluenesulfonate salt 80 g of (R)-2-[(R)-1-(5-Methyl-furan-2-yl)-propylamino]-2-phenyl-ethanol are dissolved in 160 ml of EtOH and the reaction mixture obtained is cooled to 5°. 40% methylamine in 23.5 ml of $H_2O$ are added and 70 g of sodium peroxide dissolved in 400 ml of $H_2O$ are added dropwise over a period of 1.5 hours at 5°. The reaction mixture obtained is stirred for 1.5 hours at rt, filtered and the filtrate obtained is washed with TBME, $H_2O$ and brine and the organic portion is dried over $Na_2SO_4$, filtered and solvent is evaporated. A residue obtained is dissolved in 80 ml of THF and is added dropwise to a solution of para-toluenesulfonic acid in 150 ml of THF at 0°. The reaction mixture obtained is stirred for 1 hour at rt, 200 ml of TBME are added and stirring is continued overnight. A solid is obtained and collected by filtration, washed with TBME and dried. The title compound is obtained.

f.) (R)-1-(5-Methyl-tetrahydrofuran-2-yl)-propylamine, para-toluenesulfonate salt A stirring mixture of 1.5 g of (R)-1-(5-methyl-furan-2-yl)-propylamine, para-toluenesulfonate salt and 10% Pd on 300 mg of carbon in 100 ml of MeOH is hydrogenated at 0.35 bar above atmospheric pressure at rt overnight. A reaction mixture obtained is filtered through Celite® (filter material) to remove the catalyst and solvent is evaporated.
The title compound is obtained.

Intermediate C ((R)-1-((2R,5R)-5-methyl-tetrahydrofuran-2-yl)-propylamine para-toluenesulfonate salt a.) [(R)-1-(5-Methyl-furan-2-yl)-propyl]-carbamic acid tert-butyl ester An ice-cooled solution of 591 mg of (R)-1-(5-methyl-furan-2-yl)-propylamine PTSA salt (prepared according to the procedure described in US 2004/0209946 page 19) and 0.264 ml of $Et_3N$ in 4 ml of dry MeCN are treated with 456 mg of BOC anhydride at rt under an inert atmosphere of nitrogen. A reaction mixture obtained is stirred at 0° for 30 minutes and allowed to warm to rt. Solvent is evaporated, a residue obtained is dissolved in 20 ml EtOAc and washed with 10 ml of 1M HCl, 10 ml of $Na_2SO_4$, 10 ml of brine, dried and solvent is evaporated. A solid obtained is dissolved in a minimal volume of EtOH and triturated with EtOAc/diethyl ether. The title compound is obtained. MH+ 332.

b.) [(R)-1-(2R,5R)-(5-Methyl-tetrahydrofuran-2-yl)-propyl]-carbamic acid tert-butyl ester 55 mg of 10% Pd/C is added to a solution of 453 mg of [(R)-1-(2R,5R)-(5-methyl-furan-2-yl)-propyl]-carbamic acid tert-butyl ester in 20 ml of dry MeOH at it under an inert atmosphere of nitrogen. A mixture obtained is placed under a positive atmosphere of hydrogen and stirred vigorously. Catalyst is removed by filtration and from a filtrate obtained solvent is evaporated. The title compound is obtained as a mixture of two diastereomers.

c.) ((R)-1-((2R,5R)-5-methyl-tetrahydrofuran-2-yl)-propylamine para-toluenesulfonate salt To an ice-cooled solution of 416 mg of [(R)-1-(2R,5R)-(5-methyl-tetrahydrofuran-2-yl)-propyl]-carbamic acid tert-butyl ester in 4 ml of dry DCM is added 200 μl of TFA under an inert atmosphere of nitrogen. After stirring for 3 hours, a mixture obtained is diluted with 15 ml EtOAc and washed with saturated aqueous $Na_2CO_3$. The organic portion is dried and 147 mg of para-toluenesulfonic acid are added. After stirring, solvent is evaporated. The title compound is obtained.

Intermediate D (R)-5-Aminomethyl-dihydro-furan-2-one (for Ex. 10)

A solution of 1.0 g of (R)-5-Hydroxy-piperidin-2-one in 20 ml of conc. HCl is heated at reflux for 5 hours. Solvent is evaporated and a residue obtained is triturated with EtOH.
The title compound is obtained. $MH^+$ 116.

Intermediate E

3-Amino-N,N-diethyl-2-hydroxy-benzamide a.) N,N-Diethyl-2-hydroxy-3-nitro-benzamide 1.19 ml of DIPEA are added to a stirring dispersion of 0.5 g 3-nitrosalicylic acid and 1.14 g of HATU in 4 ml of DMF at rt under an inert atmosphere of nitrogen. After stirring at it for 1 minute, 0.31 ml of diethylamine in 1 ml of dry DMF are added. After stirring at it for 1 hour, a reaction mixture obtained is added to 50 ml of 1M HCl and extracted with 50 ml EtOAc. Solvent is evaporated and a residue obtained is purified by chromatography on silca eluting with 2:1 iso-hexane/EtOAc. The title compound is obtained. $MH^+$ 239.

b.) 3-Amino-N,N-diethyl-2-hydroxy-benzamide 20 mg of 10% Pd/C are added to a solution of 127 mg of N,N-diethyl-2-hydroxy-3-nitro-benzamide in 10 ml EtOH at it under an inert atmosphere of nitrogen. A mixture obtained is placed under a positive atmosphere of hydrogen and stirred vigorously overnight. Catalyst is removed by filtration and solvent from a filtrate obtained is evaporated. A crude residue obtained is purified by chromatography on silica eluting with EtOAc.

The title compound is obtained. $MH^+$ 209

The invention claimed is:

1. A compound of formula

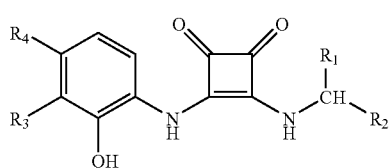

wherein $R_1$ is hydrogen or $(C_{1-8})$alkyl, and $R_2$ is a non-aromatic 5-membered unsubstituted or one- or morefold substituted heterocyclic ring system having 1 to 4 heteroatoms selected from O, S; or $R_1$ and $R_2$ together with the —CH group to which they are attached form a non-aromatic 5-membered unsubstituted or one- or morefold substituted heterocyclic ring system having 1 to 4 heteroatoms selected from O, S, $R_3$ is hydrogen, halogen, cyano, $(C_{1-8})$alkyl, $(C_{1-8})$alkoxy, amino, $(C_{1-8})$alkylamino, di$(C_{1-8})$alkylamino, $(C_{1-8})$alkylaminocarbonyl, di$(C_{1-8})$alkylaminocarbonyl, aminosulfonyl, $(C_{1-8})$alkylaminosulfonyl, di$(C_{1-8})$alkylaminosulfonyl, $(C_{1-8})$alkylsulfonyl, heterocyclylcarbonyl or heterocyclylsulfonyl, wherein heterocyclyl is a 5 or 6 membered unsubstituted or one- or morefold substituted ring system having 1 to 4 heteroatoms selected from N, O, S, $R_4$ is hydrogen, halogen or cyano;

or a pharmaceutically acceptable salt thereof.

2. A compound of claim 1 of formula (I), wherein $R_1$ is hydrogen, methyl or ethyl, and $R_2$ is a non-aromatic 5-membered unsubstituted or one- or morefold substituted heterocyclic ring system having 1 heteroatom selected from O, S; or $R_1$ and $R_2$ together with the —CH group to which they are attached form a non-aromatic 5-membered unsubstituted or onefold substituted heterocyclic ring system having 1 heteroatom selected from O, S, wherein the substituent is methyl or oxo, $R_3$ is hydrogen, di$(C_{1-2})$alkylaminocarbonyl, di$(C_{1-4})$alkylaminosulfonyl, $(C_{1-2})$alkylsulfonyl, heterocyclylcarbonyl or heterocyclylsulfonyl, wherein heterocyclyl is a 5 or 6 membered unsubstituted or one or morefold substituted ring system having 1 to 2 heteroatoms selected from N, O, $R_4$ is hydrogen or chloro or a pharmaceutically acceptable salt thereof.

3. A compound of formula (I) of claim 1 or 2 selected from the group consisting of 3-{3,4-Dioxo-2-[(tetrahydrofuran-2-ylmethyl)-amino]-cyclobut-1-enylamino}-2-hydroxy-N,N-dimethyl-benzamide, 6-Chloro-2-hydroxy-N,N-dimethyl-3-{2-[(R)-1-((2R,5R)-5-methyl-tetrahydrofuran-2-yl)-propylamino]-3,4-dioxo-cyclobut-1-enylamino}-benzenesulfonamide, 6-Chloro-2-hydroxy-N,N-dimethyl-3-{2-[(R)-1-((2R,5R)-5-methyl-tetrahydrofuran-2-yl)-propylamino]-3,4-dioxo-cyclobut-1-enylamino}-benzenesulfonamide, 3-[3,4-Dioxo-2-(tetrahydrothiophen-3-ylamino)-cyclobut-1-enylamino]-2-hydroxy-N,N-dimethyl-benzamide, 6-Chloro-3-[3,4-dioxo-2-(tetrahydrothiophen-3-ylamino)-cyclobut-1-enylamino]-2-hydroxy-N,N-dimethyl-benzenesulfonamide, 4-{6-Chloro-3-[3,4-dioxo-2-(tetrahydrothiophen-3-ylamino)-cyclobut-1-enylamino]-2-hydroxy-benzenesulfonyl}-piperazine-1-carboxylic acid tert-butyl ester, 3-[4-Chloro-2-hydroxy-3-(morpholine-4-sulfonyl)-phenylamino]-4-(tetrahydro-thiophen-3-ylamino)-cyclobut-3-ene-1,2-dione, 3-[4-Chloro-2-hydroxy-3-(4-methyl-piperazine-1-sulfonyl)-phenylamino]-4-tetrahydro-thiophen-3-ylamino)-cyclobut-3-ene-1,2-dione, 3-(4-Chloro-2-hydroxy-phenylamino)-4-(tetrahydrothiophen-3-ylamino)-cyclobut-3-ene-1,2-dione, 3-{3,4-Dioxo-2-[((R)-5-oxo-tetrahydrofuran-2-ylmethyl)-amino]-cyclobut-1-enylamino}-2-hydroxy-N,N-dimethyl-benzamide, 3-{3,4-Dioxo-2-[(R)-(tetrahydrofuran-3-yl)amino]-cyclobut-1-enylamino}-2-hydroxy-N,N-dimethyl-benzamide, 3-{3,4-Dioxo-2-[(S)-(tetrahydrofuran-3-yl)amino]-cyclobut-1-enylamino}-2-hydroxy-N,N-dimethyl-benzamide, 2-Hydroxy-N,N-dimethyl-3-{2-[(R)-1-((2S,5S)-5-methyl-tetrahydrofuran-2-yl)-propylamino]-3,4-dioxo-cyclobut-1-enylamino}-benzamide, 4-(6-Chloro-2-hydroxy-3-{2-[(R)-1 ((2R,5R)-5-methyl-tetrahydrofuran-2-yl)-propylamino]-3,4-dioxo-cyclobut-1-enylamino}-benzene sulfonyl)-piperazine-1-carboxylic acid tert-butyl ester, 3-[4-Chloro-2-hydroxy-3-(morpholine-4-sulfonyl)-phenylamino]-4-[(R)-1-((2R,5R)-5-methyl-tetrahydrofuran-2-yl)-propylamino]-cyclobut-3-ene-1,2-dione, 6-Chloro-N-ethyl-2-hydroxy-N-methyl-3-{2-[(R)-1-((2R,5R)-5-methyl-tetrahydrofuran-2-yl)-propylamino]-3,4-dioxo-cyclobut-1-enylamino}-benzenesulfonamide, 3-[4-Chloro-2-hydroxy-3-(pyrrolidine-1-sulfonyl)-phenylamino]-4-[(R)-1-((2R,5R)-5-methyl-tetrahydrofuran-2-yl)-propylamino]-cyclobut-3-ene-1,2-dione, 6-Chloro-N-ethyl-2-hydroxy-3-{2-[4(R)-1-((2R,5R)-5-methyl-tetrahydrofuran-2-yl)-propylamino]-3,4-dioxo-cyclobut-1-enylamino}-benzenesulfonamide, 3-[4-Chloro-2-hydroxy-3-(4-methyl-piperazine-1-sulfonyl)-phenylamino]-4-[(R)-1-((2R,5R)-5-methyl-tetrahydrofuran-2-yl)-propylamino]-cyclobut-3-ene-1,2-dione, 6-Chloro-N,N-diethyl-2-hydroxy-3-{2-[(R)-1-((2R,5R)-5-methyl-tetrahydrofuran-2-yl)-propylamino]-3,4-dioxo-cyclobut-1-enylamino}-benzenesulfonamide, 2-Hydroxy-N,N-dimethyl-3-{2-[(R)-1-((2R,5R)-5-methyl-tetrahydrofuran-2-yl)-propylamino]-3,4-dioxo-cyclobut-1-enylamino}-benzene sulfonamide, 6-Chloro-3-{3,4-dioxo-2-[(S)-(tetrahydrofuran-3-yl)amino]-cyclobut-1-enylamino}-2-hydroxy-N,N-dimethyl-benzene sulfonamide, N,N-Diethyl-2-hydroxy-3-{2-[(R)-1-((2R,5R)-5-methyl-tetrahydrofuran-2-yl)-propylamino]-3,4-dioxo-cyclobut-1-enylamino}-benzamide, 3-(4-Chloro-2-hydroxy-3-methanesulfonyl-phenylamino)-4-(tetrahydrothiophen-3-ylamino)-cyclobut-3-ene-1,2-dione, 3-(4-Chloro-2-hydroxy-3-methanesulfonyl-phenylamino)-4-[(R)-1-((2R,5R)-5-methyl-tetrahydrofuran-2-yl)-propylamino]-cyclobut-3-ene-1,2-dione, 3-[4-Chloro-2-hydroxy-3-(piperazine-1-sulfonyl)-phenylamino]-4-[(R)-1-((2R,5R)-5-methyl-tetrahydrofuran-2-yl)-propylamino]-cyclobut-3-ene-12-dione, 3-Chloro-2-(piperazine-1-sulfonyl)-6-(tetrahydrothiophen-3-ylamino)-phenol, 6-Chloro-N-ethyl-2-hydroxy-N-isopropyl-3-{2-[(R)-1-((2R,5R)-5-methyl-tetrahydrofuran-2-yl)-propylamino]-3,4-dioxo-cyclobut-1-enylamino}-benzenesulfonamide, 2-Hydroxy-N,N-dimethyl-3-{2-[(R)-1-((2R,5R)-5-methyl-tetrahydrofuran-2-yl)-propylamino]-3,4-dioxo-cyclobut-1-enylamino}-benzamide, 3-[4-Chloro-2-hydroxy-3-(4-isopropyl-piperazine-1-sulfonyl)-phenylamino]-4-[(R)-1-((2R,5R)-5-methyl-tetrahydrofuran-2-yl)-propylamino]-cyclobut-3-ene-1,2-dione, 3-[4-Chloro-3-(4-cyclopropyl-piperazine-1-sulfonyl)-2-hydroxy-phenylamino]-4-[(R)-1-((2R,5R)-5-methyl-tetrahydrofuran-2-yl)-propylamino]-cyclobut-3-ene-1,2-dione, 3-[4-Chloro-2-hydroxy-3-(4-isopropyl-3-methyl-piperazine-1-sulfonyl)-phenylamino]-4-[(R)-1-((2R,5R)-5-methyl-tetrahydrofuran-2-yl)-propylamino]-cyclobut-3-ene-1,2-dione, 3-[3-(4-tert-Butyl-piperazine-1-sulfonyl)-4-chloro-2-hydroxy-phenylamino]-4-[(R)-1-((2R,5R)-5-methyl-tetrahydrofuran-2-yl)-propylamino]-cyclobut-3-ene-1,2-dione, 3-[4-Chloro-2-hydroxy-3-(4-propyl-piperazine-1-sulfonyl)-phenylamino]-4-[(R)-1-((2R,5R)-5-methyl-tetrahydrofuran-2-yl)-propylamino]-cyclobut-3-ene-1,2-dione, 3-[4-Chloro-3-(4-ethyl-3-methyl-piperazine-1-sulfonyl)-2-hydroxy-phenylamino]-4-[(R)-1-((2R,5R)-5-methyl-tetrahydrofuran-2-yl)-propylamino]-cyclobut-3-ene-1,2-dione, 3-[3-(5-Benzyl-2,5-diaza-bicyclo[2.2.1]heptane-2-sulfonyl)-4-chloro-2-hydroxy-phenyl-amino]-4-[(R)-1-((2R,5R)-5-methyl-tetrahydrofuran-2-yl)-propylamino]-cyclobut-3-ene-1,2-dione, 6-Chloro-2-hydroxy-N-methyl-3-{2-[(R)-14(2R,5R)-5-methyl-tetrahydrofuran-2-yl)-propyl-amino]-3,4-dioxo-cyclobut-1-enylamino}-benzenesulfonamide, and 2-Hydroxy-N,N-dimethyl-3-{2-[(R)-1-((2R,5S)-5-methyl-tetrahydrofuran-2-yl)-propylamino]-3,4-dioxo-cyclobut-1-enylamino}-benzamide;

or a pharmaceutically acceptable salt thereof.

4. A compound of claim 1, which is a compound of formula

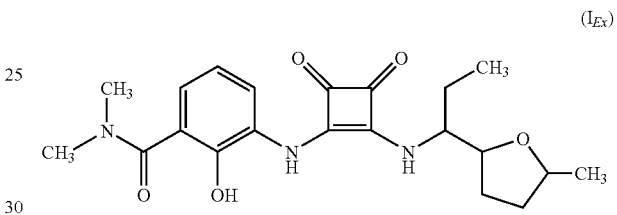

(I$_{Ex}$)

or of formula

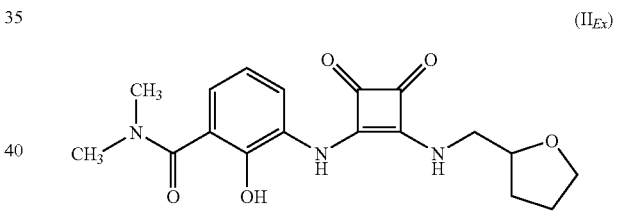

(II$_{Ex}$)

or a pharmaceutically acceptable salt thereof.

5. A pharmaceutical composition comprising a compound of claim 1 together with a pharmaceutically acceptable diluent or carrier.

6. The pharmaceutical composition of claim 5 which further comprises a co-therapeutic compound selected from an anti-inflammatory, bronchodilatory, or antihistamine drug.

* * * * *